US012416421B2

(12) United States Patent
Smith et al.

(10) Patent No.: US 12,416,421 B2
(45) Date of Patent: Sep. 16, 2025

(54) AIR PURIFIER WITH LIGHT-DEFLECTING STRUCTURE

(71) Applicant: BISSELL Inc., Grand Rapids, MI (US)

(72) Inventors: Derek Smith, Grand Rapids, MI (US); Morgan Tolles, Hastings, MI (US); Tyler Grab, Grand Rapids, MI (US)

(73) Assignee: BISSELL Inc., Grand Rapids, MI (US)

( * ) Notice: Subject to any disclaimer, the term of this patent is extended or adjusted under 35 U.S.C. 154(b) by 331 days.

(21) Appl. No.: 18/306,288

(22) Filed: Apr. 25, 2023

(65) Prior Publication Data

US 2023/0366571 A1 Nov. 16, 2023

Related U.S. Application Data

(60) Provisional application No. 63/341,610, filed on May 13, 2022.

(51) Int. Cl.
*B01D 46/60* (2022.01)
*B01D 46/10* (2006.01)
*F24F 8/108* (2021.01)
*F24F 8/167* (2021.01)
*F24F 8/22* (2021.01)
*F24F 13/20* (2006.01)

(52) U.S. Cl.
CPC .............. *F24F 8/22* (2021.01); *B01D 46/103* (2013.01); *B01D 46/60* (2022.01); *F24F 8/108* (2021.01); *F24F 8/167* (2021.01); *F24F 13/20* (2013.01)

(58) Field of Classification Search
CPC .... F24F 8/22; F24F 8/108; F24F 8/167; F24F 13/20; F24F 8/80; B01D 46/103; B01D 46/60; A61L 2209/10; A61L 2209/134; A61L 2209/14; A61L 9/20; A61L 9/205
See application file for complete search history.

(56) References Cited

U.S. PATENT DOCUMENTS

| 2,837,632 | A  | * | 6/1958 | Lipscomb  | F21V 11/06  |
|           |    |   |        |           | D26/121     |
| 7,658,891 | B1 | * | 2/2010 | Barnes    | C01B 13/11  |
|           |    |   |        |           | 128/205.28  |
| 10,894,104| B1 | * | 1/2021 | Kim       | A61L 9/20   |
| 11,291,939| B1 | * | 4/2022 | Luthe     | H04R 17/00  |
| 11,369,712| B1 | * | 6/2022 | Antonov   | A61L 9/20   |
| 11,415,332| B2 | * | 8/2022 | Lee       | F24F 8/22   |

(Continued)

*Primary Examiner* — Dung H Bui

(74) *Attorney, Agent, or Firm* — Quinn IP Law

(57) ABSTRACT

An air purifier includes an interior volume divided into upper and lower chambers, with a motorized fan assembly being positioned within the upper chamber. An ultraviolet (UV) light source is positioned within the lower chamber. A lower fan shroud includes concentric annular ribs that extend axially into the lower chamber and terminate in respective flared distal ends. The flared distal ends deflect light from the UV light source to reduce leakage of the light into the upper chamber. A diffuser can surrounds the UV light source, is affixed to the fan shroud, and has angled louvers deflecting the light to further reduce leakage thereof. Embodiments include a cylindrical media basket surrounding the diffuser can and having a media material disposed therein or thereon. The louvers are oriented to direct the light from the UV light source toward the media material.

18 Claims, 12 Drawing Sheets

(56) References Cited

U.S. PATENT DOCUMENTS

| | | | |
|---|---|---|---|
| 11,672,882 B1* | 6/2023 | Oberdorff | A61L 9/205 422/121 |
| 2008/0019861 A1* | 1/2008 | Silderhuis | F24F 8/192 422/4 |
| 2009/0041617 A1* | 2/2009 | Lee | A61L 2/208 422/4 |
| 2010/0108998 A1* | 5/2010 | Verjans | F21V 11/06 257/40 |
| 2011/0011112 A1* | 1/2011 | Goel | F24F 8/22 29/890.03 |
| 2011/0142725 A1* | 6/2011 | Liu | A61L 9/205 422/186 |
| 2019/0240371 A1* | 8/2019 | Benedek | B01D 53/8675 |
| 2019/0376711 A1* | 12/2019 | Mun | F04D 29/462 |
| 2020/0166225 A1* | 5/2020 | Goswami | B01J 35/39 |
| 2020/0268927 A1* | 8/2020 | Asano | F24F 1/00 |
| 2020/0289968 A1 | 9/2020 | Scholten et al. | |
| 2020/0298167 A1* | 9/2020 | Jeon | B01D 46/0013 |
| 2021/0187152 A1* | 6/2021 | Watanabe | B01J 35/39 |
| 2021/0228762 A1* | 7/2021 | Eide | A61L 9/205 |
| 2021/0387125 A1 | 12/2021 | Scholten et al. | |
| 2021/0402040 A1* | 12/2021 | Botts | A61L 9/20 |
| 2021/0402043 A1* | 12/2021 | Ke | A61L 9/20 |
| 2022/0040363 A1* | 2/2022 | Ling | A61L 9/20 |
| 2022/0062810 A1 | 3/2022 | Scholten et al. | |
| 2022/0125963 A1* | 4/2022 | Choi | A61L 2/22 |
| 2022/0152541 A1* | 5/2022 | Lewis | F24F 8/80 |
| 2022/0176291 A1* | 6/2022 | Yang | A61L 9/014 |
| 2022/0184540 A1* | 6/2022 | Park | F24F 3/056 |
| 2022/0184543 A1* | 6/2022 | Choi | B01D 46/0049 |
| 2022/0266174 A1* | 8/2022 | Tanyildiz | B01D 46/0028 |
| 2022/0275150 A1* | 9/2022 | Niemiec | C08G 81/00 |
| 2022/0339573 A1* | 10/2022 | Seo | B01D 46/0043 |
| 2022/0347338 A1* | 11/2022 | Greene | A61L 9/20 |
| 2022/0378971 A1* | 12/2022 | Wu | B60H 3/0078 |
| 2023/0071996 A1* | 3/2023 | Yang | F24F 8/108 |
| 2023/0175719 A1* | 6/2023 | Murray | A61L 9/20 96/224 |
| 2024/0042090 A1* | 2/2024 | Cheng | H01T 23/00 |

\* cited by examiner

AIR PURIFIER WITH LIGHT-DEFLECTING STRUCTURE

CROSS-REFERENCE TO RELATED APPLICATIONS

This application claims priority to and the benefit of U.S. Provisional Application Ser. No. 63/341,610 filed on May 13, 2022, which is hereby incorporated by reference in its entirety.

TECHNICAL FIELD

The subject disclosure pertains to air purifiers of types operable for drawing ambient air through one or more layers of filter media and irradiating the filtered air with ultraviolet light to inactivate microorganisms present in the filtered airstream.

BACKGROUND

Air purifiers of the forced-air type typically include a structural housing containing a motorized fan assembly and a filter media cartridge. When energized, fan blades of the fan assembly rotate at a high rate of speed sufficient for drawing ambient airflow into the housing. The intake airflow passes through the internal volume of the housing where it is filtered through one or more types of filter media. The level of filtration provided by a given air purifier varies with the construction of the resident filter media. For instance, high-efficiency particulate air (HEPA) filters are a popular choice due to the capability of such filter media to effectively eliminate common airborne allergens and pollutants such as pet dander, pollen, smoke particles, mold spores, bacteria, and dust mites. The airflow in some types of air purifiers is also deodorized via the process of vapor adsorption, typically by directing the airflow through an activated carbon wrap or media bed before ultimately discharging the filtered, purified, and deodorized air back into the surrounding ambient.

In addition to particulate filters and carbon-based adsorption media, some air purifiers are originally equipped with an ultraviolet (UV) light source. Irradiation of the airflow with short-wave UV-C light in particular helps inactivate suspended airborne microorganisms and pathogens by destroying their constituent DNA composition. The UV treatment process may be expedited using a suitable photocatalytic oxidizer material such as titanium dioxide ($TiO_2$) or zinc oxide (ZnO). The resulting germicidal effect of irradiating an intake airstream with UV-C light enables an appropriately sized air purifier, working in conjunction with the above-described HEPA or other filter media, to effectively clean the air of a treated room.

BRIEF SUMMARY

An air purifier as described herein is equipped with an ultraviolet (UV) light source. The UV light source is positioned within a housing where it is surrounded by internal light-deflecting structure. As the name implies, the internal light-deflecting structure collectively minimizes vertical and horizontal leakage of light from the housing to the surrounding ambient. In the various possible configurations, the UV light source is concentrically aligned with a cylindrical filter element within, with the UV light source and the filter element both situated within an airflow path. The cylindrical filter element can surround the UV light source in one or more embodiments.

While attendant benefits of treating intake airflow with UV light are briefly summarized above, those skilled in the art will also appreciate the need to carefully limit a user's personal exposure to UV light in general, and to short-wave UV-C light in particular. To that end, the UV-equipped air purifier described in detail herein may be equipped with several different internal light-deflecting features that collectively limit leakage of UV and visible light from the housing, including vertical leakage through a vented top surface of the housing through which clean air is ultimately discharged, as well as horizontal leakage through side walls of the housing.

In addition to the concentric UV light source and filter element described below, the air purifier may include a divider plate situated within an interior volume of the housing. The divider plate or other suitable structure separates the interior volume into oppositely disposed upper and lower chambers, with the upper chamber containing a motorized fan assembly therein. As used herein, the terms "upper" and "lower" refer to the relative position of the respective chambers with respect to a normal upright orientation of the air purifier. In other words, the upper chamber is situated directly above the lower chamber when the air purifier is securely resting on a floor or another stable horizontal surface. Intake air that is drawn into the lower chamber by operation of the motorized fan assembly is filtered via the filter element located within the lower chamber. The filtered air then passes into the upper chamber. The motorized fan assembly situated in the upper chamber ultimately discharges the clean air from the upper chamber to the surrounding ambient air through the vented top surface of the housing.

More particularly, light shielding structure is provided within the above-summarized air purifier using any or all of (1) a modified lower fan shroud having an elongated louvered geometry, (2) a diffuser can that is configured for use with the above-noted UV light source, and/or (3) a cylindrical media basket constructed as set forth below. While options (1), (2), and (3) when used together are expected to provide the greatest light shielding benefits, nothing precludes the use of options (1), (2), or (3) individually or in pairs, i.e., options (1) and (2), options (1) and (3), or options (2) and (3). The fan shroud, which is securely mounted to the housing, e.g., through a center opening of the divider plate or using another suitable mounting approach, protrudes into the lower chamber. As appreciated by those skilled in the art, a typical fan shroud is situated almost entirely within the upper chamber ("upper fan shroud") to support and protect the motorized fan assembly. In contrast, the present approach extends the fan shroud ("lower fan shroud") well into the lower chamber, where the lower fan shroud performs the specific light-deflecting functions described below. The diffuser can in turn surrounds the UV light source and is securely and permanently connected to the lower fan shroud to help protect the UV light source in a cage-like manner. The diffuser can thus performs a UV and visible light-deflecting function apart from that of the above-summarized lower fan shroud.

In accordance with one or more exemplary embodiments, the air purifier may include the housing and the divider plate, with the latter being positioned within the interior volume of the housing such that the divider plate separates the interior volume of the housing into the upper and lower chambers as noted above. The motorized fan assembly is positioned within the upper chamber. A UV light source is positioned within the lower chamber along with a lower fan shroud, with the lower fan shroud being connected to the divider plate or integrally formed therewith.

The lower fan shroud includes concentric annular ribs extending axially into the lower chamber and terminating in respective flared distal ends. The flared distal ends as envisioned herein are angled, shaped, sized, or otherwise configured to function as light deflectors, and thus are configured to guide or deflect UV and visible light in a first manner so as to reduce vertical leakage of light into the upper chamber.

In the various implementations described below, the diffuser can surrounds the UV light source and is affixed to the lower fan shroud. Angled louvers of the diffuser can, which are functionally analogous to the above-noted flared distal ends of the lower fan shroud, are configured to deflect emitted light in a second manner to reduce the vertical leakage of UV and visible light into the upper chamber.

The air purifier may optionally include the above-noted cylindrical media basket. The cylindrical media basket surrounds the diffuser can and includes an application-suitable media material, such as but not limited to a photocatalytic oxidizer (PCO) wrap or bed. In such an embodiment, the angled louvers of the diffuser can may be oriented upward or downward to direct the emitted light from the UV light source toward the media material.

The cylindrical media basket in one or more embodiments defines a network of closed cells, e.g., polygonal cells or honeycomb cells. Each of the cells has a respective boundary wall containing a volume of the media material in a pelletized or granular form. In other embodiments, a wire mesh is coated or impregnated with the media material.

An aspect of the disclosure includes the individual closed cells having a corresponding center axis, with the respective boundary wall being disposed at a tilt angle relative to the center axis. The tilt angle is configured to deflect transmission of light in a horizontal direction within the lower chamber, thereby reducing horizontal leakage of the light through side walls of the housing, e.g., through perforations thereof The air purifier in some configurations also includes a cylindrical filter element that coaxially surrounds the diffuser can. The filter element may include a high-efficiency particulate air (HEPA) filter media in one or more embodiments, e.g., pleated media sheets formed from a labyrinthian network of layered borosilicate microfibers or fibers of another suitable construction. The filter element may be configured as a single open-ended (SOE) filter cartridge, i.e., a cylindrical cartridge having an annular end cap disposed on one distal end that opens to the inner diameter of the filter cartridge, as appreciated in the art, and a solid closed end cap on the opposing distal end. Such a configuration ensures that airflow passes through the outer diameter of the filter cartridge to the inner diameter and is ultimately exhausted from the lower chamber through the annular/open end cap.

A light diffusing assembly is also disclosed herein for use with an air purifier constructed having a UV light source and a housing, with the housing defining separate upper and lower chambers, and with the upper chamber containing a motorized fan assembly as summarized above. The light diffusing assembly in one or more embodiments includes a lower fan shroud positioned in the lower chamber and having multiple concentric annular ribs. Each rib extends axially into the lower chamber and terminates in a flared distal end, such that the respective flared distal ends of the ribs are configured to reduce vertical leakage of light from the UV light source into the upper chamber. The light diffusing assembly also includes a diffuser can configured to surround the UV light source. The diffuser can includes angled louvers. In conjunction with the respective flared distal ends of the concentric annular ribs, such louvers reduce vertical leakage of UV light and visible light into the upper chamber via light deflection as noted above.

The cylindrical media basket may include multiple arcuate wall sections interconnected at least in part by a pair of annular end caps. The arcuate wall sections can be joined together by an optional interlocking feature arranged along or formed integrally with respective edges of the arcuate wall sections.

An aspect of the disclosure includes a socket retainer connected to or formed integrally with the lower fan shroud, and configured to support an electrical socket suitable for powering the UV light source. At least one of the concentric annular ribs in such an embodiment may define an electrical conduit configured to contain an electrical wire for powering the electrical socket.

In another aspect of the disclosure, a media basket kit is provided for use with the above-summarized air purifier. The media basket kit includes a plurality of arcuate wall sections each comprising a lattice of closed cells, an interlocking feature arranged along or formed integrally with the arcuate wall sections and configured to interconnect the arcuate wall sections into a cylindrical media basket, and a media material. The media material is arranged within and/or surrounding the closed cells. Each respective one of the closed cells has a corresponding center axis and a boundary wall disposed at a tilt angle relative to the corresponding center axis, with the tilt angle being configured to deflect transmission of light from the UV light source within the air purifier and thereby minimize horizontal leakage of the light.

The interlocking feature may optionally include a tongue-and-groove connection, a snap-fit connection, and/or a pair of annular end caps in various implementations.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

BRIEF DESCRIPTION OF THE DRAWINGS

The drawings described herein are for illustrative purposes only, are schematic in nature, and are intended to be exemplary rather than to limit the scope of the disclosure.

The appended drawings are not necessarily to scale, and may present a somewhat simplified representation of various preferred features of the present disclosure as disclosed herein, including, for example, specific dimensions, orientations, locations, and shapes. Details associated with such features will be determined in part by the particular intended application and use environment.

DETAILED DESCRIPTION

The subject disclosure may be embodied in many different forms. Representative examples are shown in the various drawings and described in detail below, with the understanding that the described embodiments are an exemplification of the disclosed principles, and not limitations of the broad aspects of the disclosure. To that end, elements and limitations described below, but not explicitly set forth in the claims, should not be incorporated into the claims, singly or collectively, by implication, inference, or otherwise. Moreover, the drawings discussed herein may not be to scale, and are provided purely for instructional purposes. Thus, the specific and relative dimensions shown in the Figures are not to be construed as limiting.

Additionally, unless specifically disclaimed: the singular includes the plural and vice versa; the words "and" and "or" shall be both conjunctive and disjunctive; the words "any" and "all" shall both mean "any and all"; and the words "including," "containing," "comprising," "having," along with permutations thereof and similar terms, shall each mean "including without limitation." Further, the words "example" or "exemplary" are used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. Moreover, words of approximation, such as "about," "almost," "substantially," "generally," "approximately," and the like, may each be used herein in the sense of "at, near, or nearly at," or "within 0-5% of," or "within acceptable manufacturing tolerances," or any logical combination thereof, for example.

Figure 1:
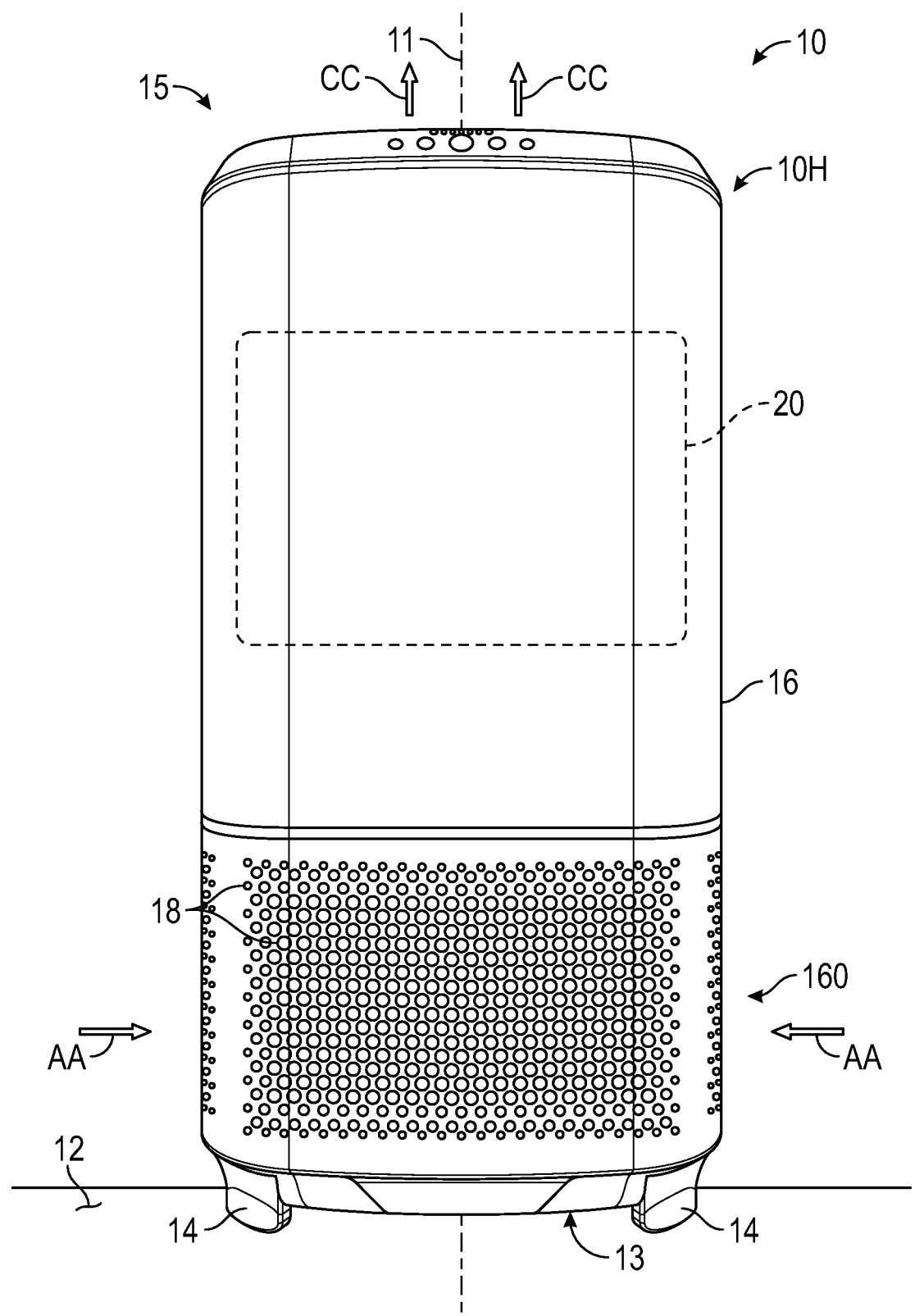
FIG. 1 is a side view illustration of an air purifier configured with ultraviolet (UV) and visible light-deflecting structural features in accordance with the present disclosure.
Figure 2:
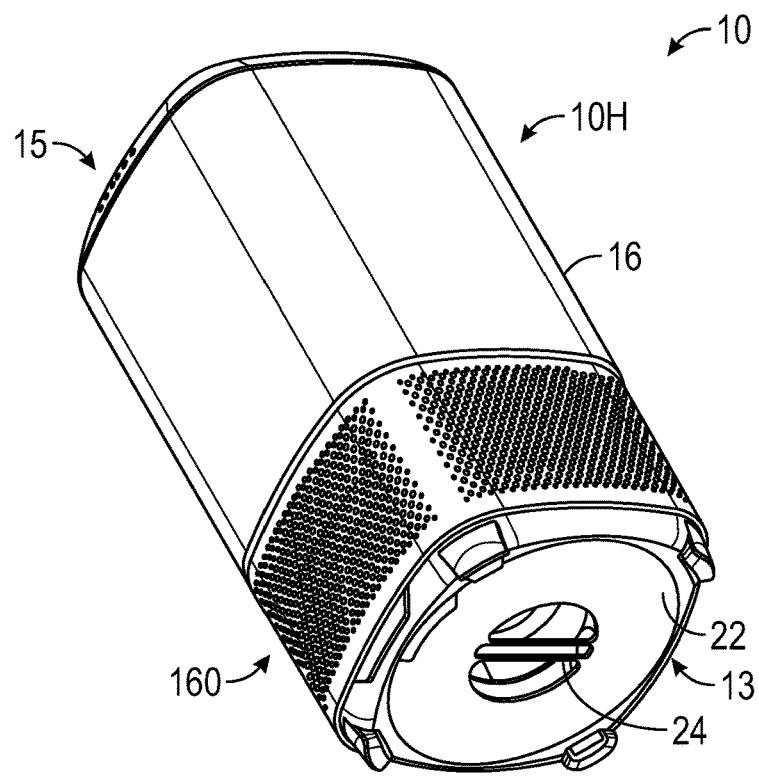
FIG. 2 is a perspective view illustration of the air purifier shown in FIG. 1 depicting side walls and a bottom access cover.
Figure 3:
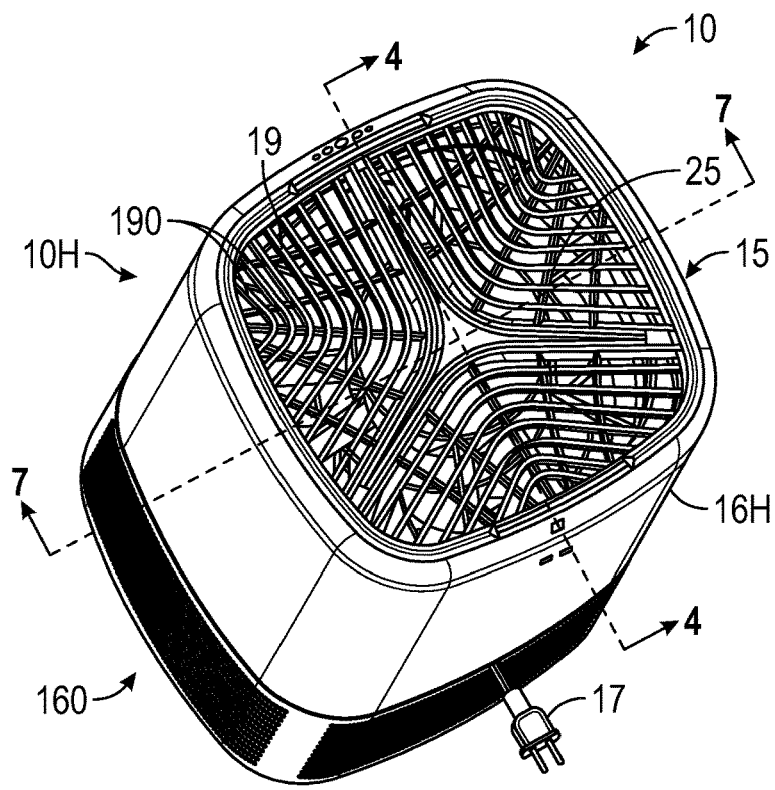
FIG. 3 is another perspective view illustration of the air purifier shown in FIGS. 1 and 2 depicting a vented top surface thereof.

Referring to the drawings, wherein like reference numbers refer to the same or like components in the several Figures, an air purifier 10 having a housing 10H is shown in FIGS. 1-3. The air purifier 10 contemplated herein may be equipped with light-deflecting structure 20, with aspects thereof described in detail below with particular reference to FIGS. 4-16. Collectively, the light-deflecting structure 20 is intended to minimize or eliminate leakage of UV light and visible light from the housing 10H to the surrounding ambient in two directions: (1) as vertical leakage through a vented top surface 15 of the housing 10H, and (2) as horizontal leakage through side walls 16 of the housing 10H. Collectively, the multifaceted construction of the light-deflecting structure 20 enables the introduction of UV light treatment of intake airflow (arrow AA) as the intake airflow passes through the housing 10H, thereby adding to the benefits of air filtration and deodorization when treating room air in a residential or commercial setting.

With reference to FIG. 1, the air purifier 10 is depicted in a normal upright position in which the air purifier 10 rests securely on a floor surface 12 or another sufficiently sturdy horizontal base. The housing 10H of the air purifier 10 may be embodied as an elongated, generally rectangular enclosure constructed, e.g., of molded plastic or another application suitable material. The housing 10H includes a longitudinal center axis 11, a closed bottom surface 13 equipped with one or more feet 14 configured to securely contact the floor surface 12, and the above-noted vented top surface 15. As used herein, "top" and "bottom" have their customary meanings relative to the depicted upright position of the air purifier 10. The respective closed bottom and vented top surfaces 13 and 15 are joined together via the side walls 16, with the side walls 16 being connected to or formed integrally with an intake base section 160. The intake base section 160, as the name implies, includes a network of air intake openings 18, e.g., equally-sized and spaced circular holes collectively allowing the intake airflow (arrow AA) to be drawn from the surrounding ambient environment into the housing 10H. Clean/treated airflow (arrows CC) is then discharged from the housing 10H through the vented top surface 15. Internal structure of the air purifier 10 is described below with reference to FIG. 4 taken along cut line 4-4, as well as FIG. 7 taken along cut line 7-7.

Referring to FIG. 2, internal access to the air purifier 10 is provided via a removable access cover 22 located on and forming part of the closed bottom surface 13. In the illustrated representative embodiment, the access cover 22 is circular in shape and includes a handle 24. To open the air purifier 10, such as when installing or replacing filter media contained therein, a user grasps the handle 24 and the side walls 16, and thereafter rotates the removable access cover 22. A quarter-turn engagement mechanism (not shown) or another suitable closure such as a threaded fitting or rotatable tabs may be used to secure the removeable access cover 22 to the housing 10H when the removeable access cover 22 is in the illustrated installed position of FIG. 2.

As best shown in FIG. 3, the vented top surface 15 of the housing 10H includes exhaust vents 19, behind which is positioned a motorized fan assembly 25. The exhaust vents 19 are defined as the open spaces between a web-like network of slat members 190, with exhaust vents 19 being sized, shaped, and otherwise configured to allow the clean airflow (arrows BB of FIG. 1) to be freely exhausted from the housing 10H to the surrounding ambient. At the same time, the exhaust vents 19 prevent ingress of fingers or smaller objects to protect users of the air purifier 10 from contacting the motorized fan assembly 25.

In a typical construction, the motorized fan assembly 25 is embodied as a polyphase/alternating current (AC) electrical device, and thus has a power plug 17 configured to connect to a typical AC wall outlet or another offboard power supply. Although omitted from the Figures for illustrative clarity, the air purifier 10 may be equipped with a circuit board or control panel operable for controlling an ON/OFF state of the air purifier 10, fan speed selection, display features/brightness, and other comfort settings. Likewise, the air purifier 10 may be equipped with wireless communications functions, e.g., to allow a user to use a software application ("app") on a smart phone, tablet computer, or other computer device to communicate remotely with the air purifier 10. For instance, the air purifier 10 may be configured to monitor air quality, including possible monitoring of volatile organic compounds (VOCs), and to provide the user with indoor air quality readings in real-time.

Figure 4:
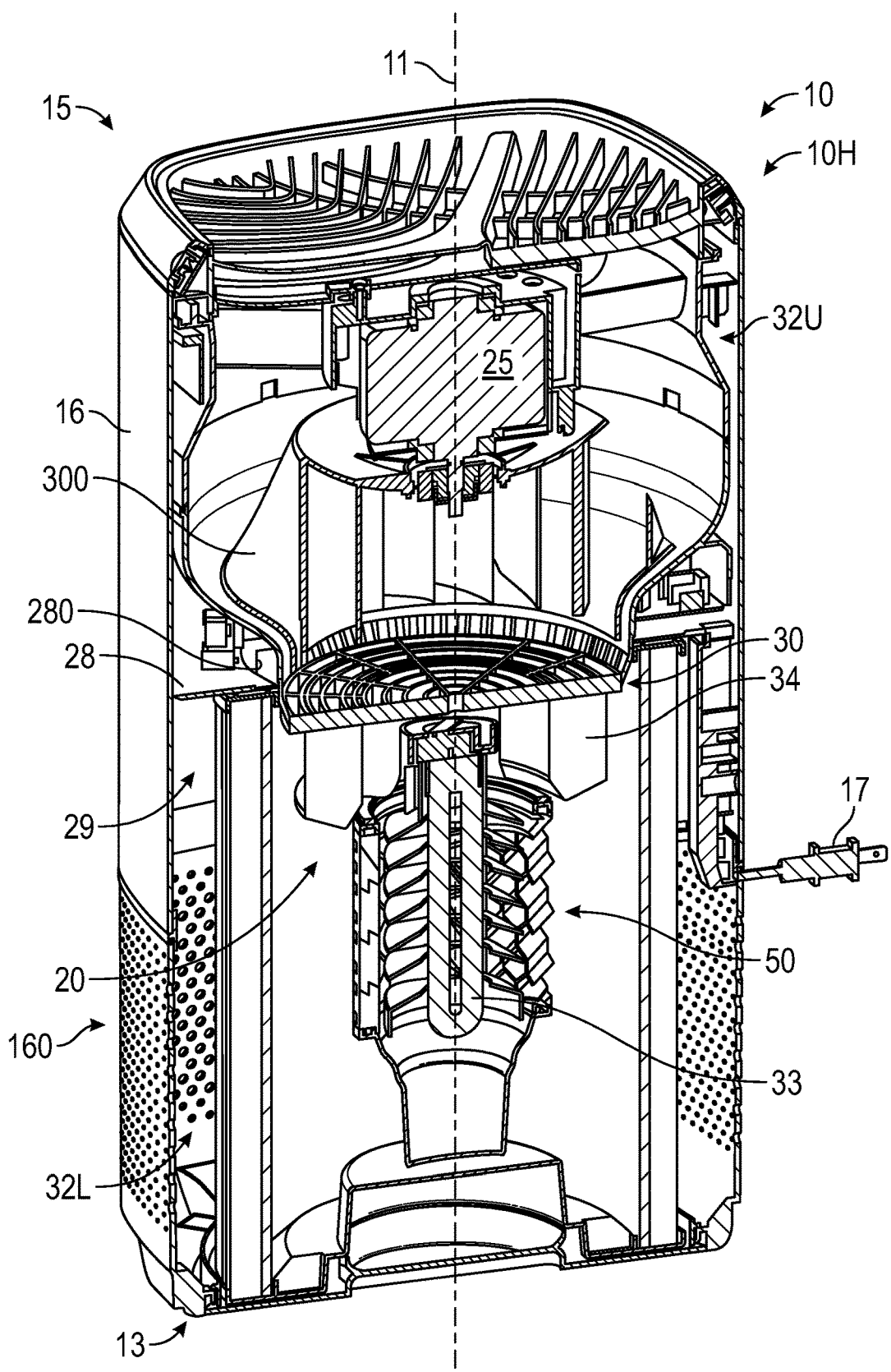
FIG. 4 is a cross-sectional perspective view illustration of the air purifier shown in FIGS. 1-3.

Referring now to FIG. 4, which is a cross-sectional illustration of the air purifier 10 of FIG. 1 taken along cut line 4-4, the housing 10H of the air purifier 10 shown in FIGS. 1-3 surrounds and thus defines an interior volume 29. A divider plate 28, e.g., a planar piece of sufficiently rigid molded plastic, may be positioned within the interior volume 29 such that the divider plate 28 separates the interior volume 29 into an upper chamber 32U and a lower chamber 32L. An ultraviolet (UV) light source 33 is positioned within the lower chamber 32L. Therefore, substantially all of the above-noted light-deflecting internal structure 20 shown schematically in FIG. 1 is contained within the lower chamber 32L, with the motorized fan assembly 25 for its part being positioned within the upper chamber 32U.

LOWER FAN SHROUD (30): The light-deflecting internal structure 20 of the present disclosure includes a lower fan shroud 30, with "lower" in this case referring to the location of the lower fan shroud 30 within the lower chamber 32L. In a possible embodiment, the lower fan shroud 30 is securely connected to the divider plate 28. An upper fan shroud 300 that is situated in the upper chamber 32U acts as a shroud in the sense of surrounding or enveloping the motorized fan assembly 25. Thus, the upper fan shroud 300 is configured to connect to the housing 10H, support the weight of the motorized fan assembly 25, and protect the motorized fan assembly 25 from damage.

The lower fan shroud 30 for its part extends through and/or is connected to the divider plate 28 in the illustrated embodiment, e.g., around a perimeter edge of a circular center opening 280 defined by the divider plate 28. In accordance with the present disclosure, the lower fan shroud 30 includes concentric annular ribs 34 that protrude axially into the lower chamber 32L, i.e., along the longitudinal center axis 11 of the air purifier 10, with the ribs 34 collectively deflecting or guiding some of the UV light emitted by the UV light source 33, e.g., a U-shaped or elongated UV-C bulb, which in turn is situated within the lower chamber 32L.

Figure 5:
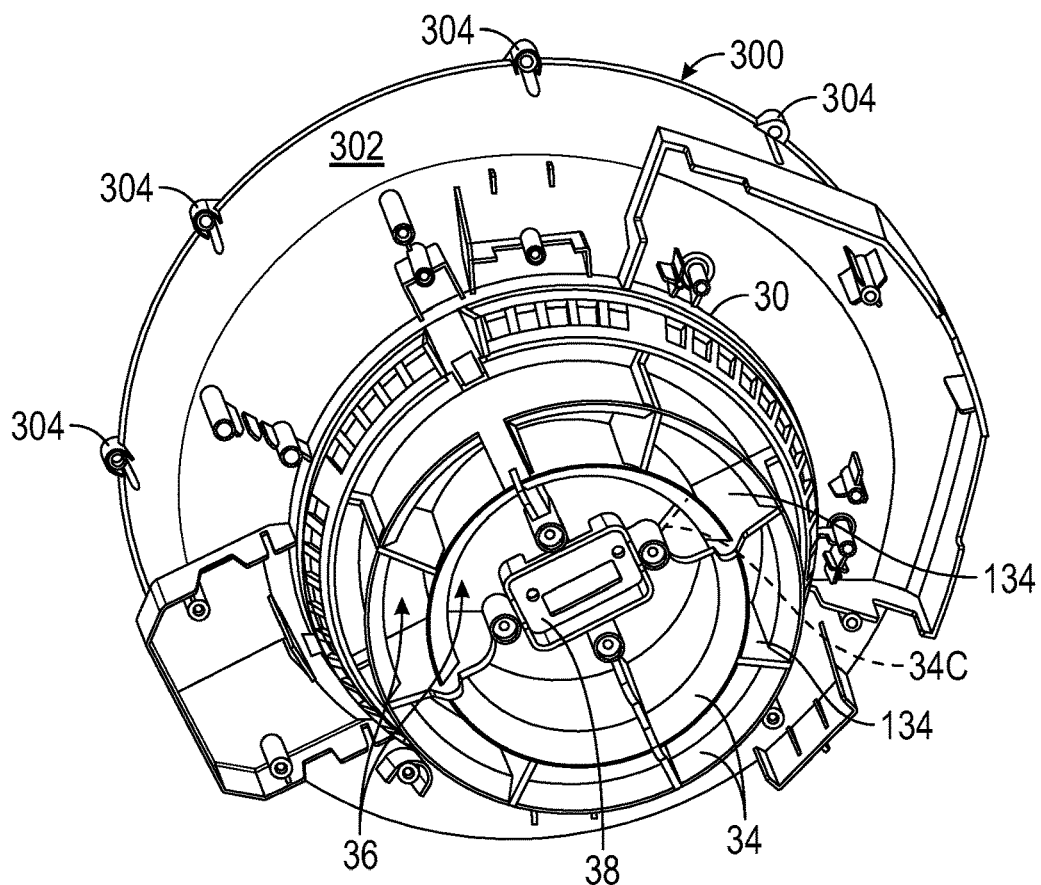
FIG. 5 is a perspective view illustration of a lower fan shroud configured in accordance with the present disclosure.
Figure 6:
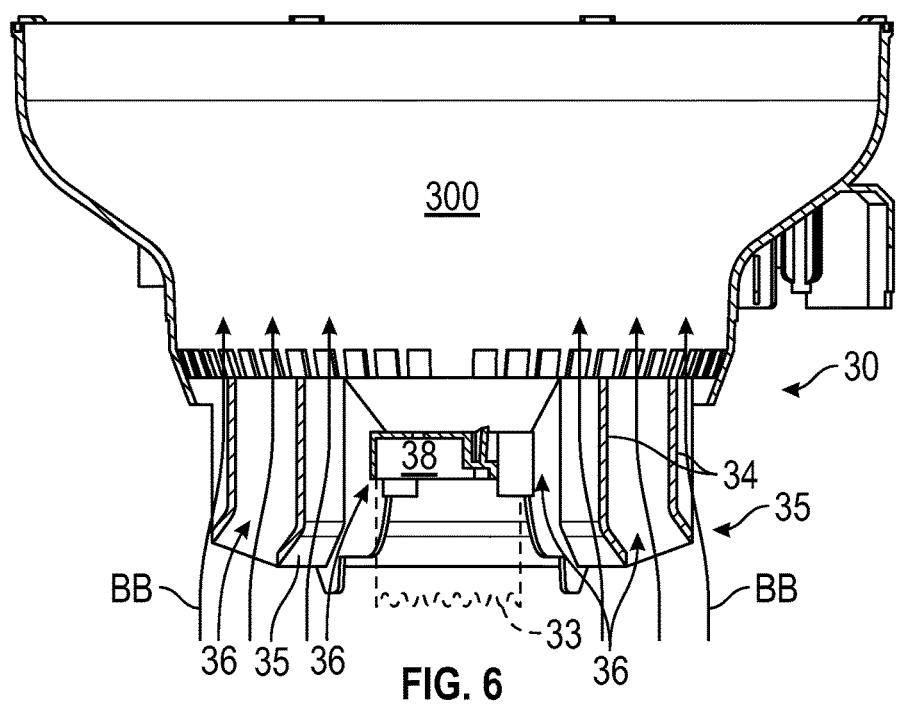
FIG. 6 is a cross-sectional side view illustration of the lower fan shroud depicted in FIG. 5.

Referring briefly to FIGS. 5 and 6, which together illustrate the lower fan shroud 30 of FIG. 4, the concentric annular ribs 34 are connected to each other or are integrally formed, and are reinforced by radial arms 134. The annular ribs 34 terminate in respective flared distal ends 35. For instance, the upper fan shroud 300 may have a bowl-like shell 302 with perimeter mounts 304 that facilitate connection to the divider plate 28 of FIG. 4. The respective flared distal ends 35 are configured, i.e., sized, shaped, and angled, so as to deflect UV light from the UV light source 33 in a first manner. This construction in turn has the benefit of reducing leakage of UV light into the upper chamber 32U of FIG. 4. In the illustrated construction, arcuate gaps 36 allow airflow (arrows BB) to pass freely through the lower fan shroud 30 and thereby improve the overall operating efficiency of the motorized fan assembly 25 shown in FIG. 4.

In certain embodiments, the lower fan shroud 30 may include and/or support a socket retainer 38. For instance, the socket retainer 38 may be securely connected to or formed integrally with the lower fan shroud 30. The socket retainer 38 can be configured to support an electrical socket (not shown) suitable for delivering electrical power to the UV light source 33 of FIG. 4, thereby causing the UV light source 33 to emit UV light. Optionally, at least one of the concentric annular ribs 34 may define or be connected to an electrical conduit 34C configured to contain therein an electrical wire (not shown) for powering the above-noted electrical socket.

Figure 7:
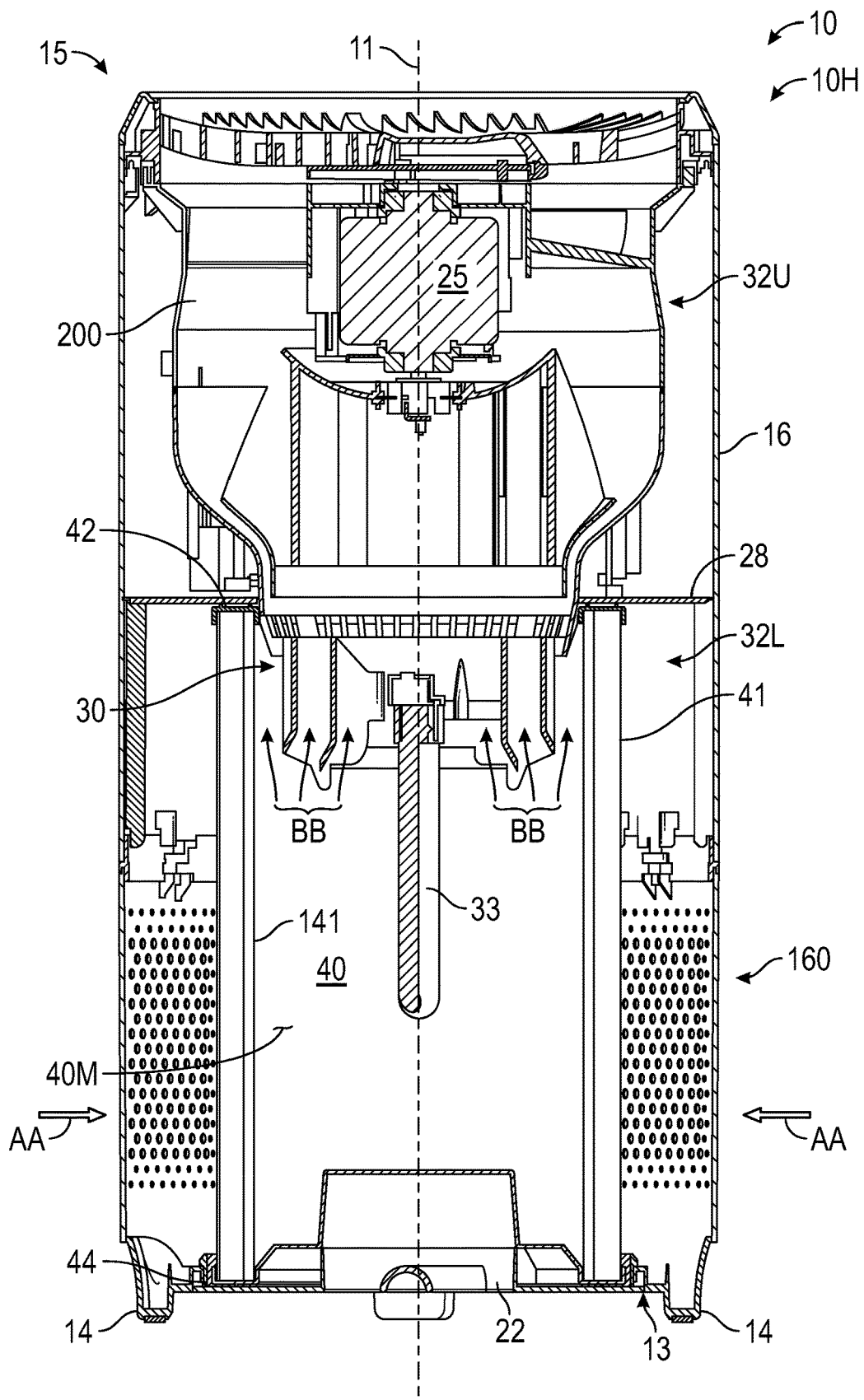
FIG. 7 is a cross-sectional side view of the air purifier shown in FIGS. 1-4, with a diffuser can of the air purifier removed for illustrative clarity.
Figure 8:
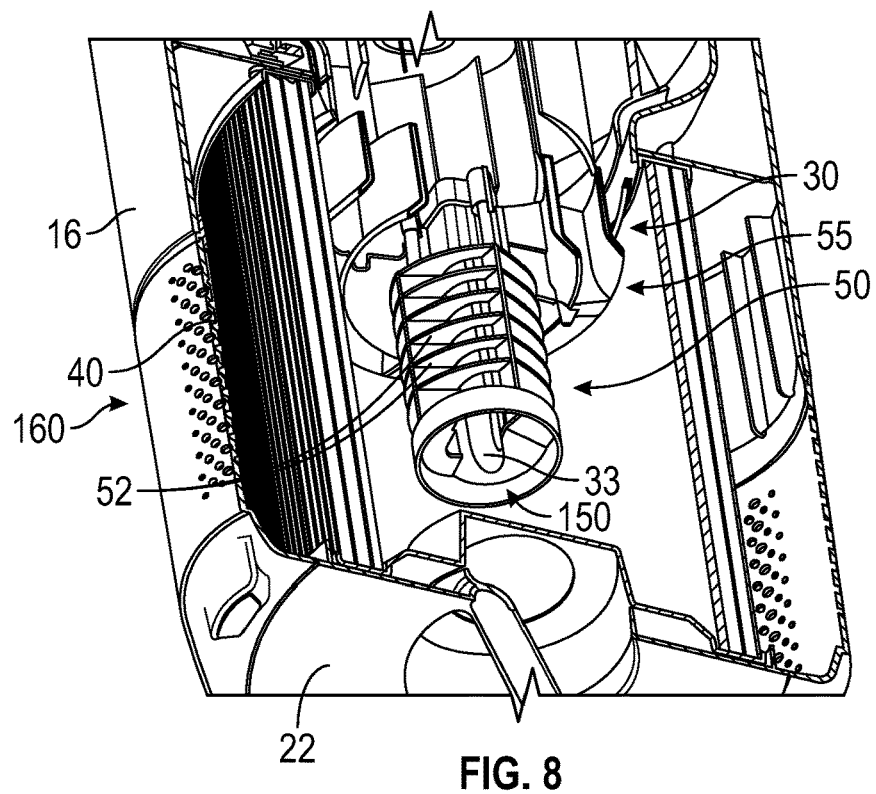
FIGS. 8 and 9 are cross-sectional perspective bottom and side view illustrations of a diffuser can in accordance with the present disclosure.

FILTER ELEMENT (40): FIG. 7, which is a cross-sectional view taken along cut line 7-7 of FIG. 1, illustrates a particular construction of the air purifier 10 in which a filter element 40 installed within the lower chamber 32L of the housing OH surrounds the UV light source 33. The filter element 40 and the UV light source 33 are thus coaxially aligned with the longitudinal center axis 11. The UV light source 33 is shown in an installed position with respect to the above-described lower fan shroud 30. Air filtering. UV treatment, and odor reduction functions performed by the air purifier 10 therefore occur within the lower chamber 32L. For illustrative clarity, FIG. 7 omits additional aspects of the light-deflecting structure 20 of FIG. 1, specifically a diffuser can 50, which is described in detail below with reference to FIGS. 8 and 9.

In the embodiments described herein, the filter element 40 is a cylindrical single open-ended (SOE) cartridge as shown, with the SOE cartridge including one or more types of filter media 40M. For example, the filter media 40M may include a high-efficiency particulate air (HEPA) filter layer, an odor-reducing carbon media layer, and a prefilter layer, all of which are understood in the art, along with sufficient structural retainers, netting, etc. In this exemplary configuration, an open end 42 of the SOE cartridge securely seals against the divider plate 28 while a closed end cap 44 is positioned adjacent to the removeable access cover 22. As described above, such a removeable access cover 22 may be removed to access the lower chamber 32L, e.g., in the event it becomes necessary to replace the filter element 40 and/or the UV light source 33.

The inlet airflow (arrows AA) drawn into the lower chamber 32L by operation of the motorized fan assembly 25 situated within the upper chamber 32U is forced through the filter element 40, flowing from an outer diameter surface 41 of the filter element 40 to its inner diameter surface 141. As the UV light source 33 is disposed radially within the filter element 40 and thus within an airflow path within the housing 10H, a portion of the filtered airflow (arrows BB) passes in proximity to the UV light source 33 before passing into the upper chamber 32U, which allows the filtered airflow (arrows BB) to be irradiated and purified by UV-C light from the UV light source 33 as noted above. Clean air (arrows CC of FIG. 1) that is ultimately discharged from the upper chamber 32U to the surrounding ambient via the vented top surface 15 is therefore effectively filtered and UV-treated within the scope of the present disclosure.

DIFFUSER CAN (50): As noted above, the light-deflecting structure 20 (FIG. 1) may include a diffuser can 50 as depicted in the partial cross-sectional view of FIG. 8. The diffuser can 50 is configured to surround the UV light source 33, such that the diffuser can 50 effectively forms a cage around the UV light source 33. In a contemplated embodiment, the diffuser can 50 is constructed of molded plastic or another application suitable material, and is securely affixed to the lower fan shroud 30. Due to its construction and function, the diffuser can 50 may be considered herein in some embodiments to be an extension of the lower fan shroud 30, and thus not removable. In other embodiments, however, the diffuser can 50 could be removable and sealed, e.g., via a snap fit fastener, twist lock feature, or other suitable connection. To that end, the diffuser can 50 may be securely connected at one end to the fan shroud 30, e.g., using fasteners, bonding, etc. Thus, the fan shroud 30 and the diffuser can 50 together form a light diffusing assembly 55 in some embodiments. Another end of the diffuser can 50 is open, i.e., as distal end 150, to allow a user to access and replace the UV light source 33 from underneath as needed.

Figure 9:
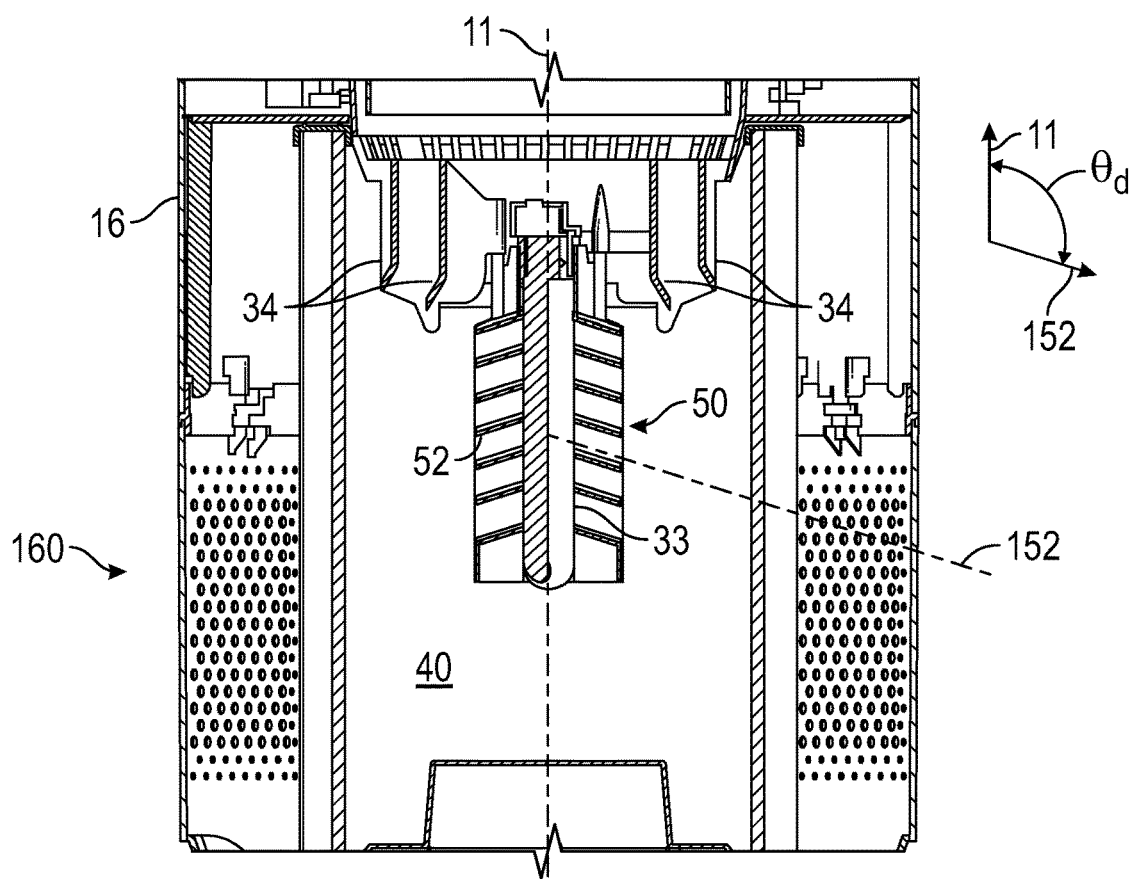

In order to effectively perform its light-deflecting functions, the diffuser can 50 includes a set of angled louvers 52. As best shown in FIG. 9, which is a cross-sectional view taken along cut line 4-4 of FIG. 1, the angled louvers 52 having a louver axis 152 oriented at a deflection angle ($0d$) relative to the longitudinal center axis 11 of the air purifier 10, such that the angled louvers 52 are collectively configured to deflect the UV light and visible light emitted by the UV light source 33 in a second manner, i.e., apart from the light-deflecting function of the above-described ribs 34 of the lower fan shroud 30. In this manner, the diffuser can 50 reduces undesirable leakage of the UV and visible into the upper chamber 32U of FIG. 4.

Figure 10:
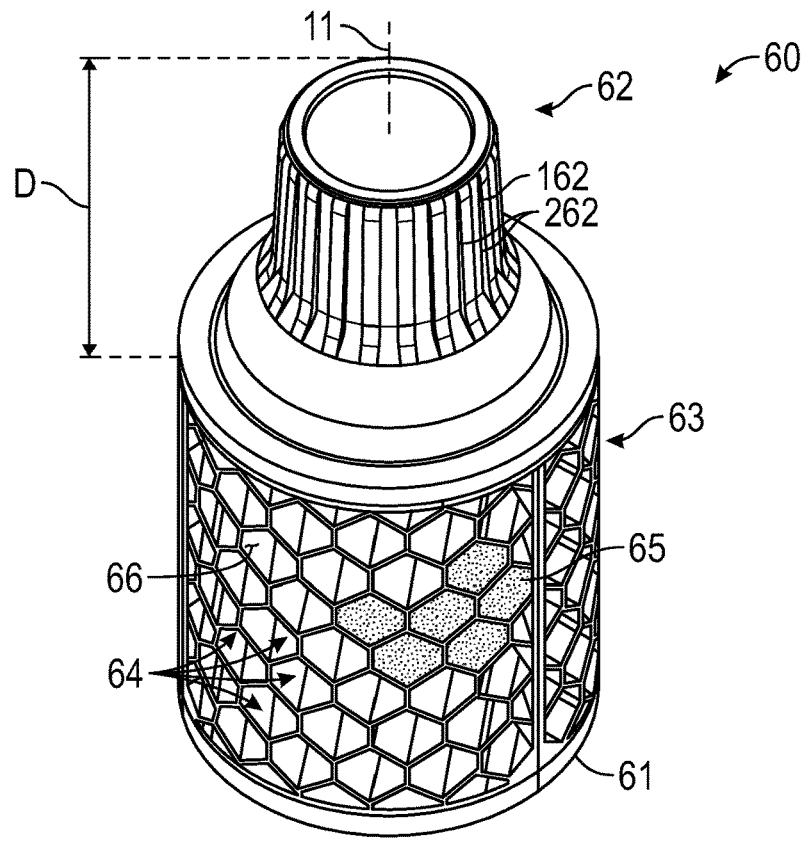
FIGS. 10 and 11 are respective perspective view illustrations of a media basket for use with the air purifier of FIGS. 1-4 defining a network of closed cells configured to contain a media material.
Figure 11:
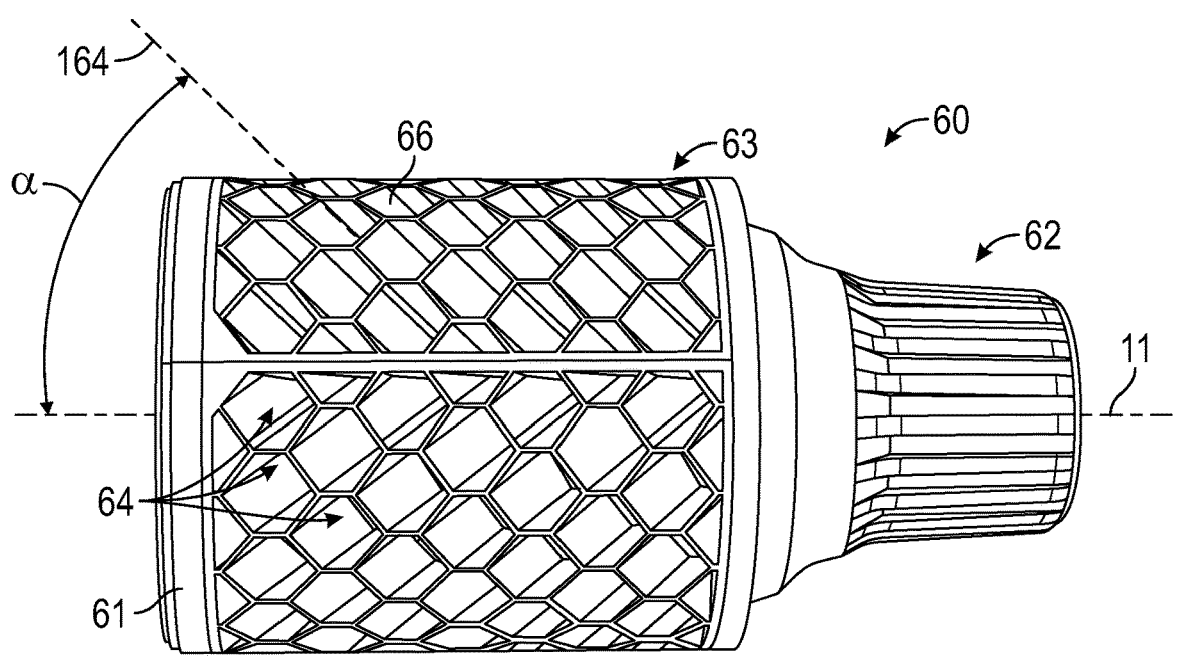
Figure 13:
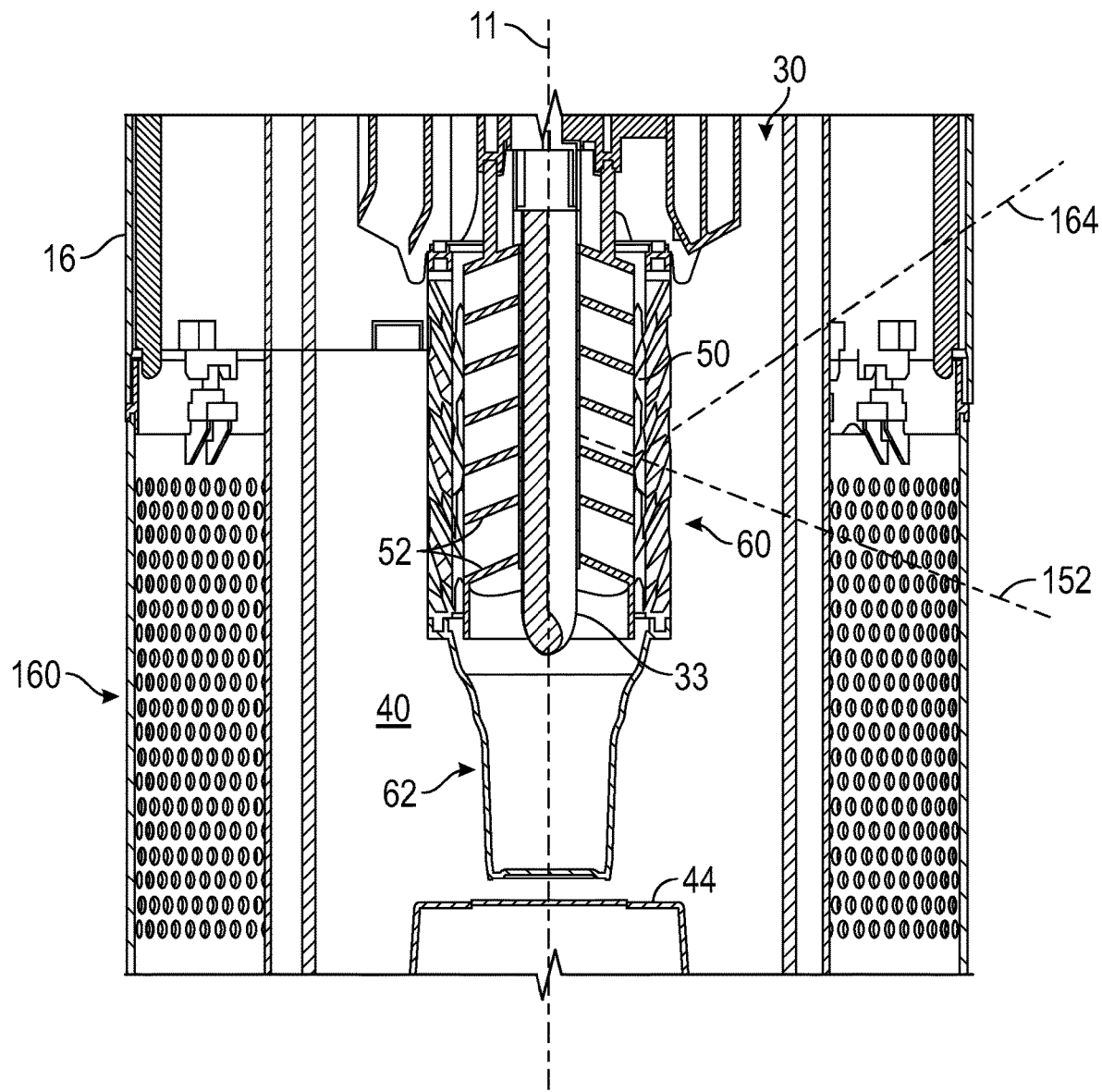
FIG. 13 is a cross-sectional side view of the air purifier shown in FIGS. 1-4 depicting aspects of the diffuser can and media basket.

MEDIA BASKET (60): Referring now to FIGS. 10 and 11, in some configurations the diffuser can 50 of FIGS. 8 and 9 operates in conjunction with a cylindrical media basket 60. In such an implementation of the present teachings, the media basket 60 surrounds the diffuser can 50. In other words, the diffuser can 50 in an installed position is coaxial with and surrounded by the media basket 60, as best shown in FIG. 13, with longitudinal center axis 11 shown in FIGS. 10 and 11 to emphasize the coaxial structure of the media basket 60, UV light source 33, filter element 40, diffuser can 50, and lower fan shroud 30 of the present disclosure.

The media basket 60 in the contemplated embodiments has an annular-shaped end cap 61, e.g., of molded silicone or another UV-stable material, an end cap 62, which is closed as opposed to the annular/ring-shaped "open" structure of the end cap 61 having a length (D) along the direction of the longitudinal center axis 11, and a media wall 63. The end cap 62 may be constructed of molded plastic in some embodiments, with the distance D possibly being sufficient to abut the removeable access cover 22 of FIG. 4, i.e., as an optional standoff feature. To facilitate rotation of the media basket 60 when installing or removing the media basket 60 to/from the air purifier 10, the end cap 62 may include a generally cylindrical knob 162 having surface ridges 262, or a knurl pattern or other surface texture enabling a user to securely grasp the end cap 62 and rotate the same about the longitudinal center axis 11.

Within the scope of the disclosure, a media material 65, e.g., a photocatalytic oxidizer (PCO) or another application-suitable media such as activated charcoal, is disposed on or within the media wall 63. As appreciated in the art, photocatalysts of the type contemplated herein, e.g., titanium dioxide ($TiO_2$) or zinc oxide (ZnO), are energized by incident UV light. To that end, the tilt angle ($0d$) of the individual angled louvers 52 of the diffuser can 50 shown in FIG. 9 can be oriented in one or more embodiments to direct UV light toward the media material 65 when treating airflow (arrows BB of FIG. 7) passing through the air purifier 10 of FIGS. 1-3.

In the representative embodiment of FIGS. 10 and 11, the media wall 63 of the cylindrical media basket 60 defines a network of closed cells 64. The closed cells 64 as shown may be polygonal, e.g., arranged in a honeycomb pattern or hexagonal. Each respective one of the closed cells 64 in turn has a respective boundary wall 66, and contains therein a volume of the media material 65 in a pelletized or granular form. For illustrative clarity, only some of the closed cells 64 are shown in FIG. 10 as being filled with the media material 65. However, those skilled in the art will appreciate that all of the closed cells 64 are typically filled with the same media material 65, which is retained within the closed cells 64 using, e.g., mesh or an air permeable wrap.

Figure 12:
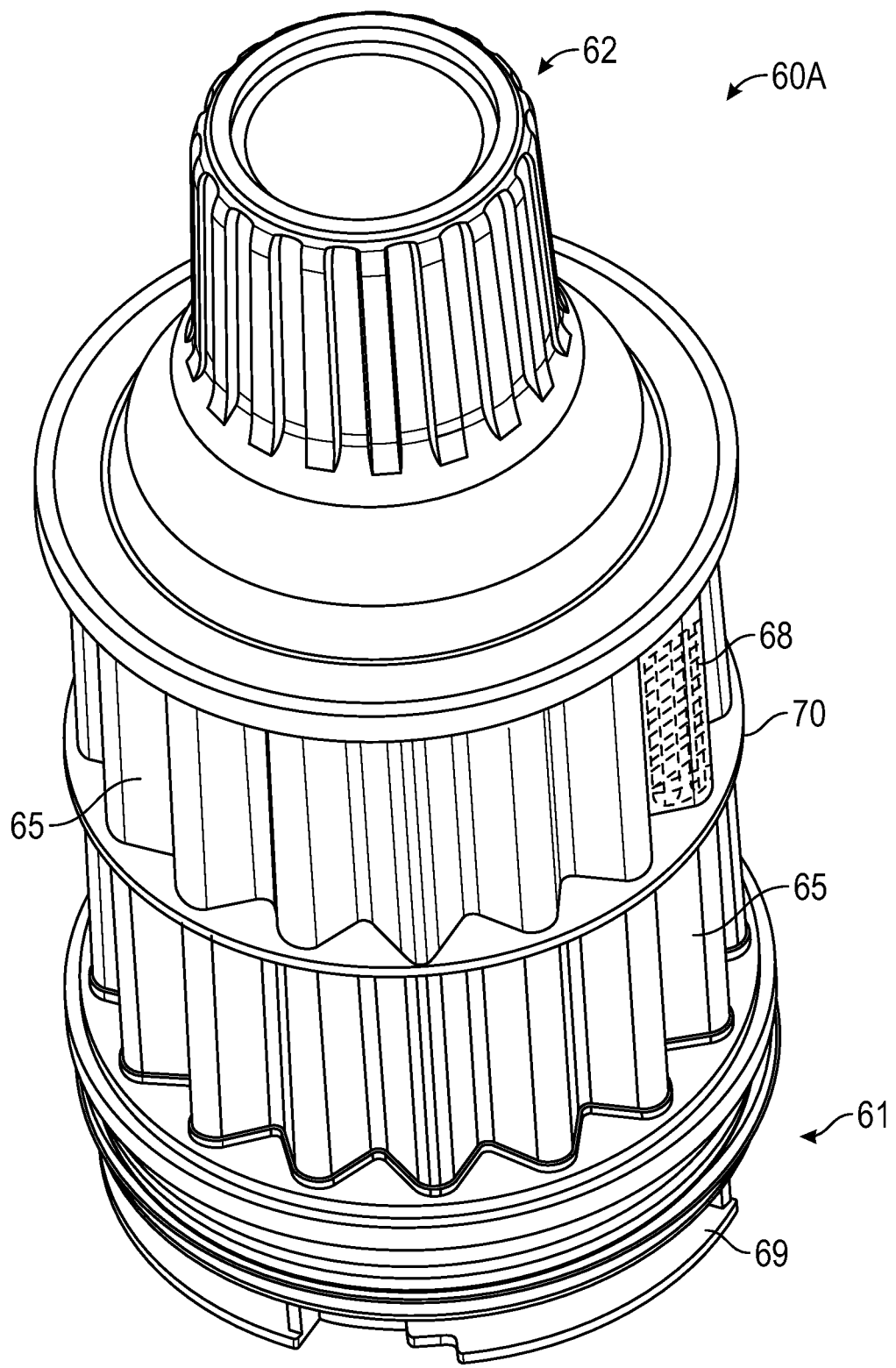
FIG. 12 is a perspective view illustration of an alternative construction of the media basket of FIGS. 10 and 11 having a wire mesh coated or impregnated with the media material.

Alternatively, a media basket 60A as shown in FIG. 12 may include a wire mesh 68 coated or impregnated with the media material 65. Such an embodiment may be corrugated or pleated as shown to maximize surface area and thus exposure of the media material 65 to incident UV light. A support ring 71 may be present at the approximate midpoint of the media basket 60A to provide additional structural support as shown. Also depicted in FIG. 12, the end cap 61 may include radial tabs 69 to enable a quarter-turn connection of the media basket 60 to the lower fan shroud 30 described above, with such structure being understood in the art.

Referring again briefly to FIG. 11, in order to optimize the light-deflecting functionality the embodiment illustrated in FIGS. 10 and 11, each of the closed cells 64 has a corresponding center axis 164, with one such center axis 164 shown in FIG. 10 for illustrative simplicity. The longitudinal center axis 164 is disposed at a non-orthogonal deflection angle α relative to the longitudinal center axis 11, such that the boundary walls 66 are oriented to deflect or otherwise limit transmission of at least some of the light from the UV light source 33 of FIGS. 8 and 9 in a horizontal direction within the lower chamber 32L of FIGS. 4 and 7. That is, each center axis 164 is not arranged perpendicular or normal to the longitudinal center axis 11, but rather is angled to deflect light emitted by the UV light source 33.

FIG. 13 depicts the installed UV light source 33, the diffuser can 50, and the media basket 60 in which the end cap 62 does not extend all the way to the closed end cap 44 of the filter element 40, advantages may be gained by arranging an upward/downward angle of inclination of the various center axes 164 opposite an upward/downward angle of inclination of the angled louvers 52 of the diffuser can 50, i.e., the louver axis 152. From the perspective of FIG. 13, for example, this means that all of the center axes 164 tilt upward and all of the louver axes 152 tilt downward.

In other implementations these two angles may be reversed, i.e., the center axes 164 may point upward and the louver axes 152 may tilt downward, or both may be angled in the same direction, albeit with corresponding different light deflecting effects. Together, cooperative angular construction of the diffuser can 50 and the media basket 60 may help minimize horizontal bleed of UV light through the side walls 16 of FIGS. 1-3. The actual deflection angle would vary with the intended application, with non-limiting/representative deflection angles including ±45° to 75° relative to the longitudinal center axis 11.

Figure 14:
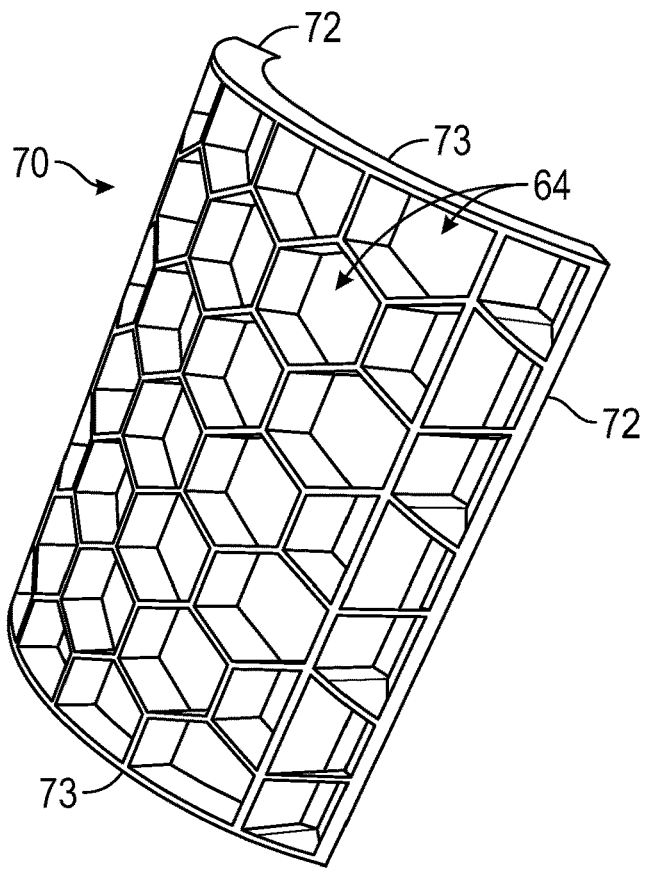
FIGS. 14, 15, and 16 are perspective view illustrations of an optional three-piece implementation of the media basket shown in FIGS. 4 and 10-13.
Figure 15:
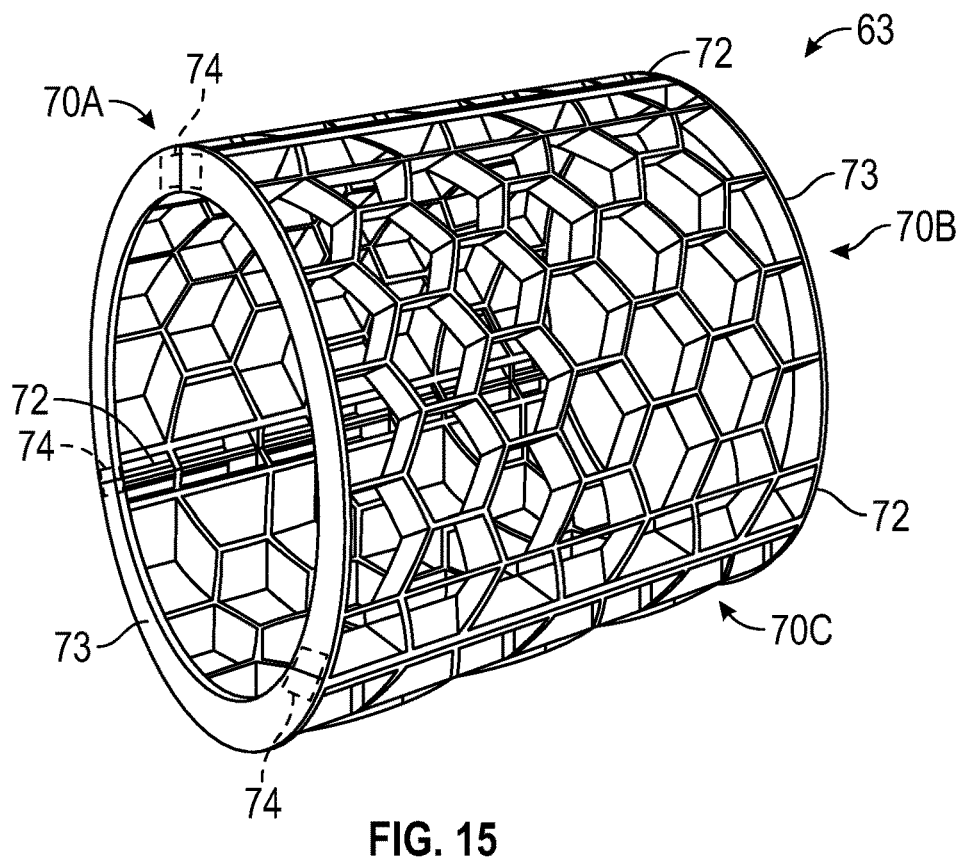

Referring now to FIGS. 14 and 15, construction of the media basket 60 of FIGS. 10 and 11 having the above-described deflection angle α would be impracticable to construct as a single piece, due largely to the non-orthogonal arrangement of the center axes 11 and 164. A possible solution is to construct the media wall 63 of FIG. 15 from multiple arcuate wall sections 70 (FIG. 14). A representative example construction is shown in FIG. 15, with the media wall 63 having three respective 120° arcuate wall sections 70A, 70B, and 70C. The arcuate wall section 70 of FIG. 14 is thus representative, with the closed cells 64 extending between lateral edges 72 of the arcuate wall section 70. Each arcuate wall section 70 therefore embodies a semi-circular honeycomb pattern in a possible construction. The arcuate wall sections 70A, 70B, and 70C of FIG. 15 are interconnected at least in part by the respective end caps 61 and 62 of FIGS. 10 and 11, such as by abutting the arcuate wall sections 70A, 70B, and 70C along edges 72 to form a cylinder, and thereafter potting or bonding the end caps 61 and 62 to radial ends 73 of the arcuate wall sections 70A, 70B, and 70C. Such an approach may be used alone or in conjunction with an interlocking feature 74 configured to securely interconnect the arcuate wall sections 70A, 70B, and 70C.

Figure 14A:
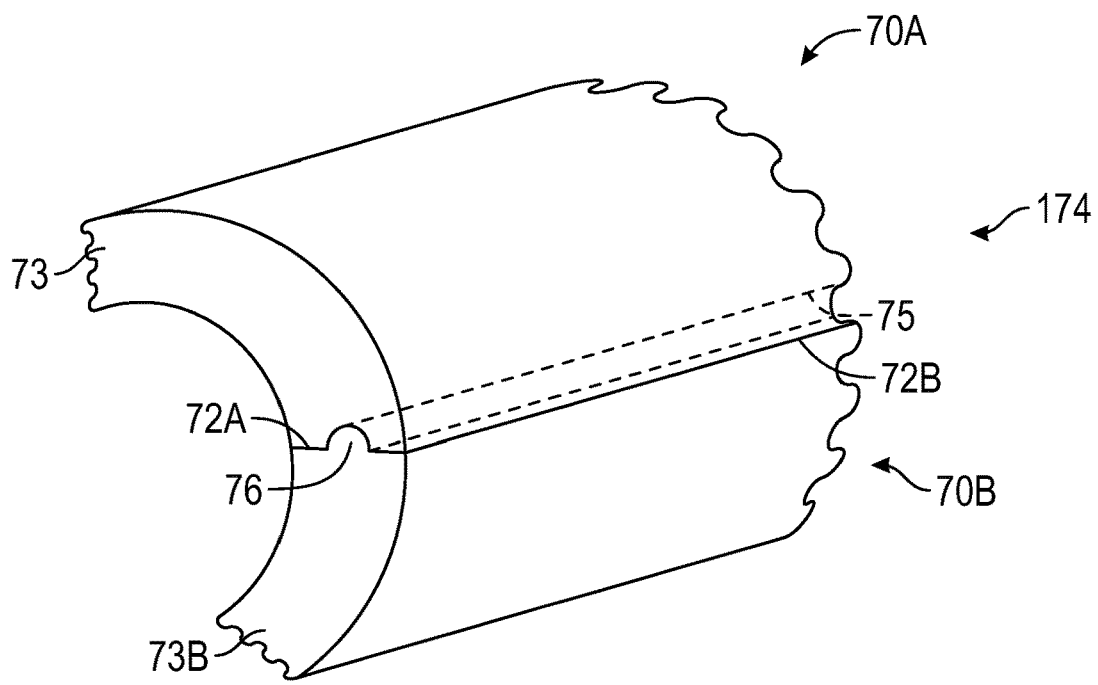
FIGS. 14A and 14B illustrate two possible edge configurations for arcuate wall sections of the media basket shown in FIGS. 14-16.
Figure 14B:
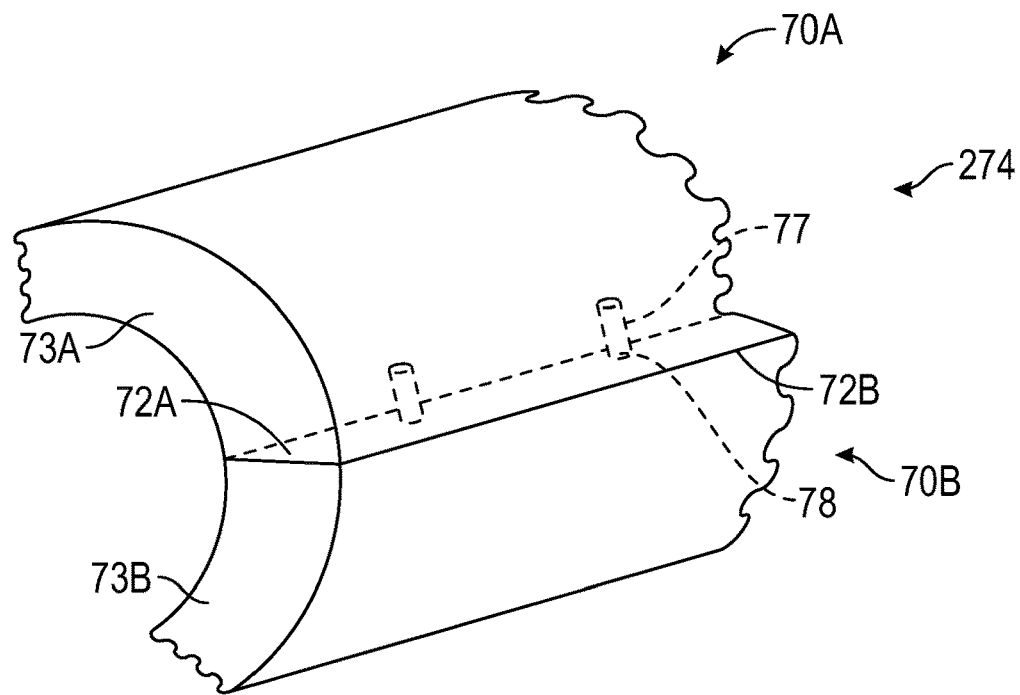

Referring briefly to FIGS. 14A and 14B, in one or more embodiments a suitable interlocking feature 174 or 274 may be arranged along or formed integrally with respective lateral edges 72A and 72B to enable adjacent wall sections 70A and 70B to engage their adjoining neighbor. Similarly configured arcuate wall section 70C of FIG. 15 is omitted for illustrative simplicity and clarity. Lateral edges 72A and 72B of adjoining arcuate wall sections 70A and 70B could be equipped with mating or engaging features that interconnect the arcuate wall sections 70A and 70B, thereby providing structural rigidity to the resulting media wall 63 of FIG. 15. For example, the interlocking feature 174 may embody a tongue-and-groove connection as shown in FIG. 14A by providing an elongated groove 75, e.g., along lateral edge 72A of arcuate wall section 70A in this instance, and an elongated tongue 76 along an adjacent lateral edge 72B of arcuate wall section 70B. Mutual engagement of the elongated tongue 76 and groove 75 thus secures adjacent lateral edges 72A and 72B.

Another possible solution is a pin-and-hole variation as shown as the interlocking feature 274 of FIG. 14B, in which one of the lateral edges 72A or 72B defines a spaced series of holes 77 and the other of the lateral edges 72A or 72B includes a spaced series of mating pins 78, e.g., cylindrical extensions. The holes 77 along lateral edge 72A in the non-limiting representative configuration of FIG. 14B thus align with the pins 78 arranged along the lateral edge 72B, thereby functioning in an alternative manner to that of the representative tongue-and-groove solution FIG. 14A. Different implementations of the interlocking feature 74 of FIG. 14 may be envisioned within the scope of the disclosure in other embodiments, and therefore the exemplary solutions of FIGS. 14A and 14B are representative of the present teachings and non-limiting thereof.

Figure 16:
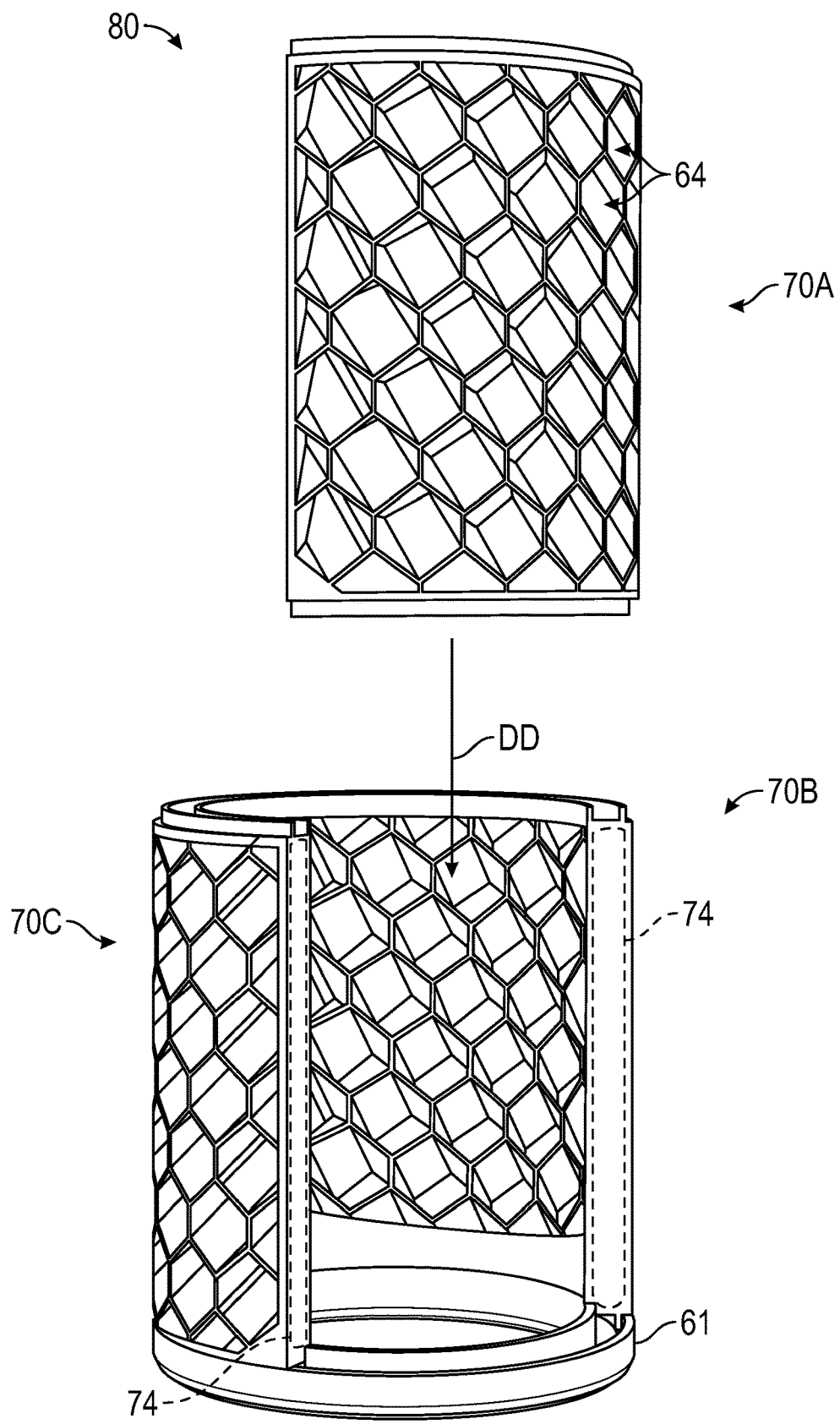

Referring to FIG. 16, an aspect of the disclosure includes a media basket kit 80 for use with the air purifier 10 of FIGS. 1-3, which in turn is equipped with the UV light source 33 as described in detail hereinabove. The media basket kit 80 in a possible embodiment includes a plurality of the arcuate wall sections 70 of FIG. 14, e.g., three equally sized 120° arcuate wall sections 70A, 70B, and 70C as shown, with each arcuate wall section 70A, 70B, and 70C comprising a lattice of closed cells 64. The optional interlocking feature 74 can be arranged along or formed integrally with the arcuate wall sections 70A, 70B, and 70C, and configured to interconnect the plurality of arcuate wall sections 70A, 70B, and 70C into the cylindrical media basket 60 of FIGS. 10 and 11.

As depicted in FIG. 16, for instance, arcuate wall sections 70B and 70C may be interconnected and set into the end cap 61, e.g., bonded thereto with silicone or another application suitable/UV-resistant material. As described above, the various closed cells 64 are filled with the PCO material 65 as shown in FIG. 10, with the PCO material 65 omitted from FIG. 16 for clarity. Thereafter, the arcuate wall section 70A may be inserted between the arcuate wall sections 70B and 70C in the direction of arrow DD and connected thereto along its edges 72. The end cap 62 of FIGS. 10 and 11 is then connected to the opposite end to complete construction of the media basket 60 depicted in FIGS. 10 and 11.

The air purifier 10 of FIG. 1 is therefore equipped with several structural features that may be used separately or in different combinations to enable UV-C light treatment, specifically from within the internal airstream, with minimal light leakage and airflow impingement. The various improvements seek to eliminate a sufficient amount of UV light bleed without restricting airflow. With respect to airflow, the light-deflecting structure 20 described above works with a coaxial/in-airstream UV light source, i.e., the UV light source 33 arranged within the airflow indicated by arrows BB of FIG. 6. Unlike constructions which seek to maximize airflow by positioning a UV light source outside of the airstream, the present solutions instead incorporate the light-deflecting structure 20 on-axis to deflect or otherwise limit light bleed while leaving sufficient space for the airflow (arrows BB) to escape the lower chamber 32L unimpeded. These and other attendant benefits will be readily appreciated by those skilled in the art in view of the foregoing disclosure.

The following Clauses provide some example configurations of the air purifiers, light diffusing assemblies, and media basket kits disclosed herein.

Clause 1: An air purifier comprising: a housing having an interior volume that is divided into an upper chamber and a lower chamber; a motorized fan assembly positioned within the upper chamber; an ultraviolet (UV) light source positioned within the lower chamber; and a lower fan shroud positioned within the lower chamber, and comprising concentric annular ribs that extend axially into the lower chamber and terminate in respective flared distal ends, wherein the respective flared distal ends are configured to deflect light from the UV light source in a first manner to thereby reduce a leakage of the light into the upper chamber.

Clause 2: The air purifier of clause 1, further comprising a cylindrical media basket having a media material disposed therein or thereon.

Clause 3: The air purifier of clauses 1 or 2, further comprising: a diffuser can surrounding the UV light source, wherein the diffuser can is affixed to the lower fan shroud and includes angled louvers arranged to deflect the light from the UV light source in a second manner to thereby reduce the leakage of the light into the upper chamber.

Clause 4: The air purifier of clause 3, further comprising a cylindrical media basket surrounding the diffuser can and having the media material disposed therein or thereon.

Clause 5: The air purifier of clauses 3 or 4, wherein the angled louvers of the diffuser can are oriented to direct the light from the UV light source toward the media material.

Clause 6: The air purifier of any of clauses 1-5, further comprising a cylindrical filter element surrounding the UV light source.

Clause 7: The air purifier of claim 6, wherein the cylindrical filter element includes a high-efficiency particulate air (HEPA) filter media.

Clause 8: The air purifier of any of clauses 2-7, wherein the cylindrical media basket defines a network of closed cells each having a respective boundary wall and containing a volume of the media material in a pelletized or granular form.

Clause 9: The air purifier of clause 8, wherein each respective closed cell of the network of closed cells has a corresponding center axis, and the respective boundary wall is disposed at an angle relative to the corresponding center axis to thereby deflect transmission of the light from the UV light source in a horizontal direction within the lower chamber.

Clause 10: The air purifier of any of clauses 2-9, wherein the media material is constructed of a wire mesh that is coated or impregnated with the media material.

Clause 11: The air purifier of any of claims 2-9, wherein the media material includes a photocatalytic oxidizer (PCO) material.

Clause 12: A light diffusing assembly for use with an air purifier having an ultraviolet (UV) light source and a housing, wherein the housing defines an upper chamber and a lower chamber, the light diffusing assembly comprising: a lower fan shroud positioned in the lower chamber and having multiple concentric annular ribs extending axially into the lower chamber and terminating in respective flared distal ends, such that the respective flared distal ends are collectively configured to reduce a leakage of light from the UV light source into the upper chamber of the housing in a first manner; and a diffuser can configured to surround the UV light source, wherein the diffuser can includes angled louvers configured, in conjunction with the respective flared distal ends of the concentric annular ribs, to reduce the leakage of the light from the UV light source into the upper chamber of the housing in a second manner.

Clause 13: The light diffusing assembly of clause 12, further comprising: a cylindrical media basket surrounding the diffuser can and containing a media material, wherein the angled louvers of the diffuser can are oriented to direct the light from the UV light source toward the media material.

Clause 14: The light diffusing assembly of clause 12, wherein the cylindrical media basket defines a network of closed cells, each respective closed cell of the network of closed cells containing a volume of the media material in a pelletized or granular form, and wherein the media material is a photocatalytic oxidizer (PCO) material.

Clause 15: The light diffusing assembly of clause 14, wherein the network of closed cells is arranged in a honeycomb pattern.

Clause 16: The light diffusing assembly of any of clauses 13-15, wherein the cylindrical media basket includes multiple arcuate wall sections and a pair of end caps, and the multiple arcuate wall sections are interconnected at least in part by the pair of end caps.

Clause 17: The light diffusing assembly of clause 16, wherein the arcuate wall sections are joined together by an interlocking feature arranged along or formed integrally with respective edges of the arcuate wall sections.

Clause 18: The light diffusing assembly of any of clauses 12-17, further comprising: a socket retainer connected to or formed integrally with the lower fan shroud and configured to support an electrical socket for powering the UV light source.

Clause 19: A media basket kit for use with an air purifier equipped with an ultraviolet (UV) light source, comprising: a plurality of arcuate wall sections each comprising a network of closed cells; an interlocking feature arranged along or formed integrally with the arcuate wall sections, and configured to interconnect the plurality of arcuate wall sections into a cylindrical media basket; and a media material arranged within and/or surrounding the closed cells, wherein each respective one of the closed cells has a corresponding center axis and a boundary wall disposed at an angle relative to the corresponding center axis, such that the boundary wall is configured to deflect light from the UV light source within the air purifier.

Clause 20: The media basket kit of clause 19, wherein the interlocking feature includes a tongue-and-groove connection or a pin-and-hole connection.

While some of the best modes and other embodiments have been described in detail, various alternative designs and embodiments exist for practicing the present teachings defined in the appended claims. Those skilled in the art will recognize that modifications may be made to the disclosed embodiments without departing from the scope of the subject disclosure. Moreover, the present concepts expressly include combinations and sub-combinations of the described elements and features. The detailed description and the drawings are supportive and descriptive of the present teachings, with the scope of the present teachings defined solely by the claims.

What is claimed is:

1. An air purifier comprising:
    a housing having an interior volume that is divided into an upper chamber and a lower chamber;
    a motorized fan assembly positioned within the upper chamber;
    an ultraviolet (UV) light source positioned within the lower chamber;
    a lower fan shroud positioned within the lower chamber, and comprising concentric annular ribs that extend axially into the lower chamber and terminate in respective flared distal ends, wherein the respective flared distal ends are configured to deflect light from the UV light source in a first manner to thereby reduce a leakage of the light into the upper chamber;
    a cylindrical filter element surrounding the UV light source; and
    a plurality of radial arms extending between and connecting the concentric annular ribs.

2. The air purifier of claim 1, wherein the cylindrical filter element includes a high-efficiency particulate air (HEPA) filter media.

3. The air purifier of claim 1, further comprising:
    a cylindrical media basket having a media material disposed therein or thereon.

4. The air purifier of claim 3, wherein the cylindrical media basket defines a network of closed cells each having a respective boundary wall and containing a volume of the media material in a pelletized or granular form.

5. The air purifier of claim 4, wherein each respective closed cell of the network of closed cells has a corresponding center axis, and the respective boundary wall is disposed at an angle relative to the corresponding center axis to thereby deflect transmission of the light from the UV light source in a horizontal direction within the lower chamber.

6. The air purifier of claim 3, wherein the media material is constructed of a wire mesh that is coated or impregnated with the media material.

7. The air purifier of claim 3, wherein the media material includes a photocatalytic oxidizer (PCO) material.

8. The air purifier of claim 3, wherein the cylindrical media basket includes multiple arcuate wall sections and a pair of end caps, and the multiple arcuate wall sections are interconnected at least in part by the pair of end caps.

9. The air purifier of claim 3, wherein the cylindrical media basket includes multiple arcuate wall sections joined together by an interlocking feature arranged along or formed integrally with respective edges of the arcuate wall sections.

10. The air purifier of claim 9, wherein the interlocking feature includes a tongue-and-groove connection or a pin-and-hole connection.

11. The air purifier of claim 3, wherein the cylindrical media basket includes an annular-shaped end cap.

12. The air purifier of claim 3, wherein the cylindrical media basket includes a closed end cap that has a cylindrical knob.

13. The air purifier of claim 1, further comprising: a diffuser can surrounding the UV light source, wherein the diffuser can is affixed to the lower fan shroud and includes angled louvers arranged to deflect the light from the UV light source in a second manner to thereby reduce the leakage of the light into the upper chamber.

14. The air purifier of claim 13, further comprising:
a cylindrical media basket surrounding the diffuser can and having a media material disposed therein or thereon.

15. The air purifier of claim 14, wherein the angled louvers of the diffuser can are oriented to direct the light from the UV light source toward the media material.

16. The air purifier of claim 1, further comprising:
a socket retainer connected to or formed integrally with the lower fan shroud and configured to support an electrical socket for powering the UV light source.

17. The air purifier of claim 1, wherein the housing includes a removable access cover located on or forming a closed bottom surface of the housing.

18. The air purifier of claim 1, further comprising:
a divider plate situated within an interior volume of the housing and separating the interior volume into the upper chamber and the lower chamber.

* * * * *